United States Patent
Gohno

(10) Patent No.: US 7,409,034 B2
(45) Date of Patent: Aug. 5, 2008

(54) RADIATION TOMOGRAPHY APPARATUS

(75) Inventor: Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/926,697

(22) Filed: Aug. 26, 2004

(65) Prior Publication Data

US 2005/0053188 A1    Mar. 10, 2005

(30) Foreign Application Priority Data

Sep. 9, 2003    (JP) .............................. 2003-317093

(51) Int. Cl.
*H05G 1/60*    (2006.01)
*A61B 6/03*    (2006.01)
*G21K 1/04*    (2006.01)

(52) U.S. Cl. .................. 378/7; 378/15; 378/19; 378/150; 378/151

(58) Field of Classification Search ............ 378/7, 378/15, 19, 146, 147, 150, 151, 152, 207
See application file for complete search history.

(56) References Cited

U.S. PATENT DOCUMENTS

| | | | | |
|---|---|---|---|---|
| 4,149,080 | A | * | 4/1979 | Schittenhelm ............. 378/7 |
| 4,286,156 | A | * | 8/1981 | Wagner ................ 250/363.02 |
| 4,352,986 | A | * | 10/1982 | Pfeiler ........................ 378/14 |
| 4,670,840 | A | | 6/1987 | Freundlich |
| 4,881,251 | A | * | 11/1989 | Nambu et al. ............... 378/7 |
| 4,897,788 | A | | 1/1990 | King |
| 4,995,107 | A | * | 2/1991 | Klingenbeck ............... 378/7 |
| 5,099,505 | A | | 3/1992 | Seppi et al. |
| 5,684,855 | A | * | 11/1997 | Aradate et al. ............ 378/4 |
| 6,023,494 | A | * | 2/2000 | Senzig et al. ............. 378/4 |
| 6,041,097 | A | * | 3/2000 | Roos et al. ............... 378/62 |
| 6,173,033 | B1 | * | 1/2001 | Klingenbeck-Regn et al. ... 378/20 |
| 6,175,609 | B1 | | 1/2001 | Edic et al. |
| 6,215,843 | B1 | | 4/2001 | Saito et al. |
| 6,320,929 | B1 | * | 11/2001 | Von Der Haar ........... 378/4 |
| 6,445,761 | B1 | * | 9/2002 | Miyazaki et al. ........... 378/8 |

(Continued)

FOREIGN PATENT DOCUMENTS

JP    09-234197    9/1997

(Continued)

OTHER PUBLICATIONS

Japanese language Notice of Reasons for Rejection.

(Continued)

*Primary Examiner*—Allen C. Ho
(74) *Attorney, Agent, or Firm*—Armstrong Teasdale LLP

(57) ABSTRACT

An apparatus for improving the tomographic image quality by preventing the tomographic image contrast from degrading and preventing artifact from occurring even if many scattered radiations occur. An X-ray detection array obtains first detection data using the X-ray detection elements corresponding to an area not shielded by a collimator. Further, the X-ray detection array obtains second detection data using the X-ray detection elements corresponding to an area shielded by the collimator. A central processing unit corrects the first detection data based on the detection data including the first and second detection data. Finally, the central processing unit generates a tomographic image for an imaging area of the imaging object.

7 Claims, 11 Drawing Sheets

U.S. PATENT DOCUMENTS

| | | | |
|---|---|---|---|
| 6,501,820 B2 * | 12/2002 | Guendel | 378/15 |
| 6,639,964 B2 * | 10/2003 | Schneider et al. | 378/7 |
| 6,687,326 B1 * | 2/2004 | Bechwati et al. | 378/7 |
| 6,876,719 B2 * | 4/2005 | Ozaki | 378/7 |
| 6,925,140 B2 * | 8/2005 | Bruder | 378/4 |
| 6,990,170 B2 * | 1/2006 | Sugihara et al. | 378/15 |
| 7,113,569 B2 * | 9/2006 | Okumura et al. | 378/150 |

FOREIGN PATENT DOCUMENTS

| | | |
|---|---|---|
| JP | 2000070254 | 3/2000 |
| JP | 2000197628 | 7/2000 |
| JP | 2001145621 | 5/2001 |

OTHER PUBLICATIONS

An English language translation of a First Office Action from the Patent Office of the People's Republic of China dated Oct. 13, 2006.

* cited by examiner

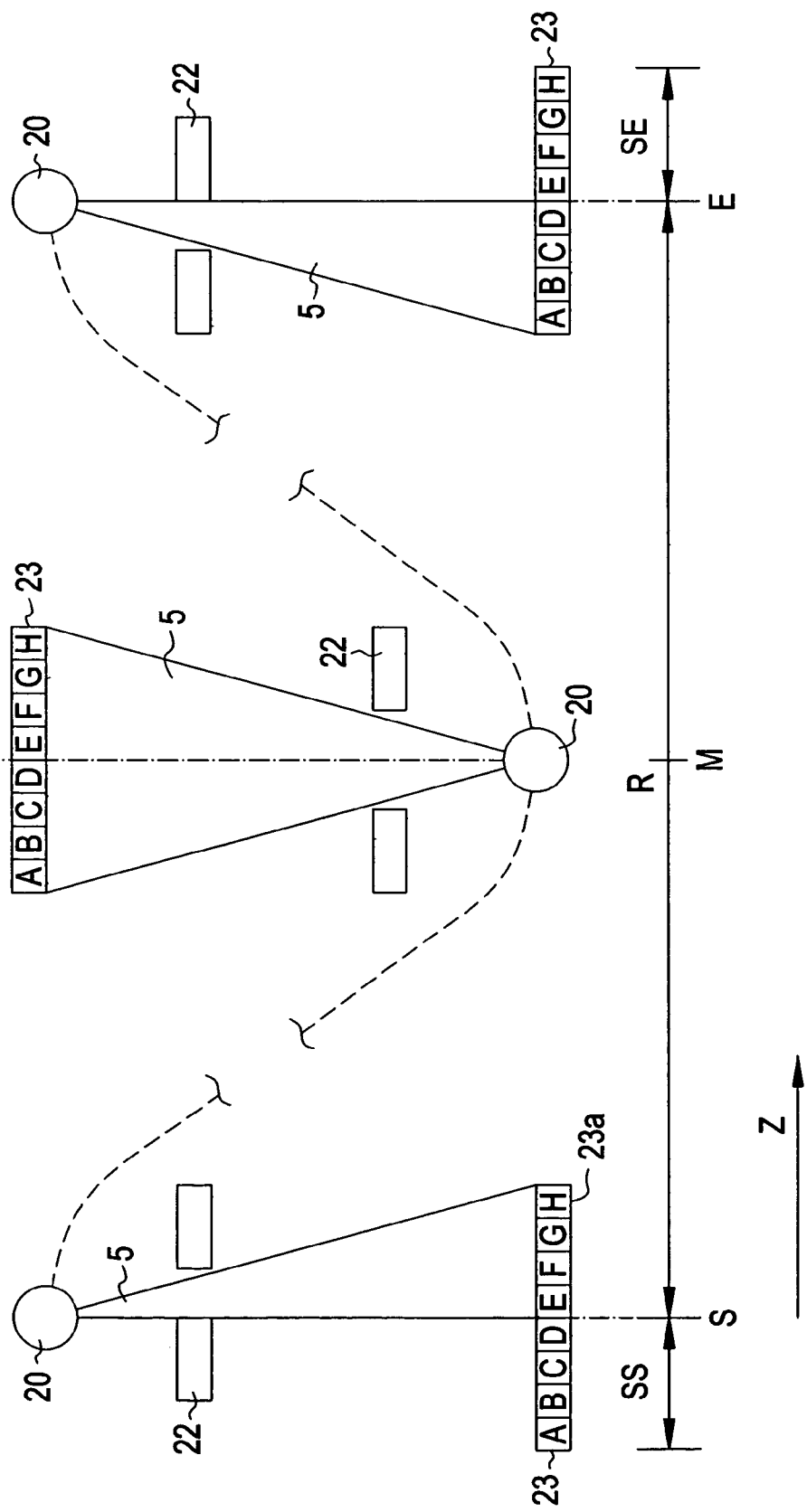

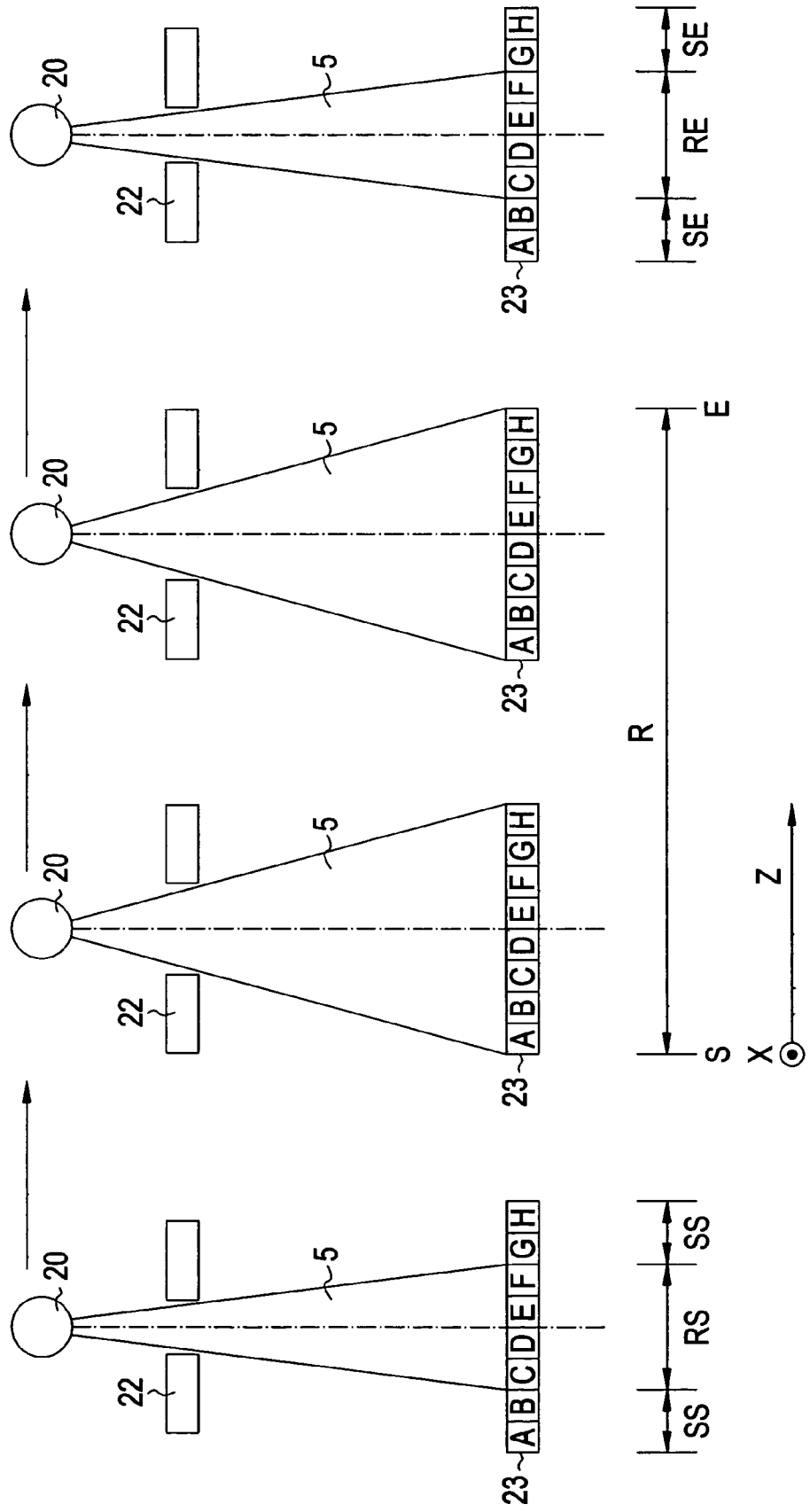

FIG. 10A

|   | A | B | C | D | E | F | G | H |   |
|---|---|---|---|---|---|---|---|---|---|
| 1 | E11 | E21 | E31 | E41 | E51 | E61 | E71 | E81 |   |
| 2 | E12 | E22 | E32 | E42 | E52 | E62 | E72 | E82 |   |
| 3 | E13 | E23 | E33 | E43 | E53 | E63 | E73 | E83 |   |
| 4 | E14 | E24 | E34 | E44 | E54 | E64 | E74 | E84 |   |
| 5 | E15 | E25 | E35 | E45 | E55 | E65 | E75 | E85 |   |
| 6 | E16 | E26 | E36 | E46 | E56 | E66 | E76 | E86 |   |
| 7 | E17 | E27 | E37 | E47 | E57 | E67 | E77 | E87 |   |
| 8 | E18 | E28 | E38 | E48 | E58 | E68 | E78 | E88 |   |

|   | A | B | C | D | E | F | G | H |
|---|---|---|---|---|---|---|---|---|
| 1 | [E'11] | [E'21] | E'31 | E'41 | E'51 | E'61 | [E'71] | [E'81] |
| 2 | [E'12] | [E'22] | E'32 | E'42 | E'52 | E'62 | [E'72] | [E'82] |
| 3 | [E'13] | [E'23] | E'33 | E'43 | E'53 | E'63 | [E'73] | [E'83] |
| 4 | [E'14] | [E'24] | E'34 | E'44 | E'54 | E'64 | [E'74] | [E'84] |
| 5 | [E'15] | [E'25] | E'35 | E'45 | E'55 | E'65 | [E'75] | [E'85] |
| 6 | [E'16] | [E'26] | E'36 | E'46 | E'56 | E'66 | [E'76] | [E'86] |
| 7 | [E'17] | [E'27] | E'37 | E'47 | E'57 | E'67 | [E'77] | [E'87] |
| 8 | [E'18] | [E'28] | E'38 | E'48 | E'58 | E'68 | [E'78] | [E'88] |

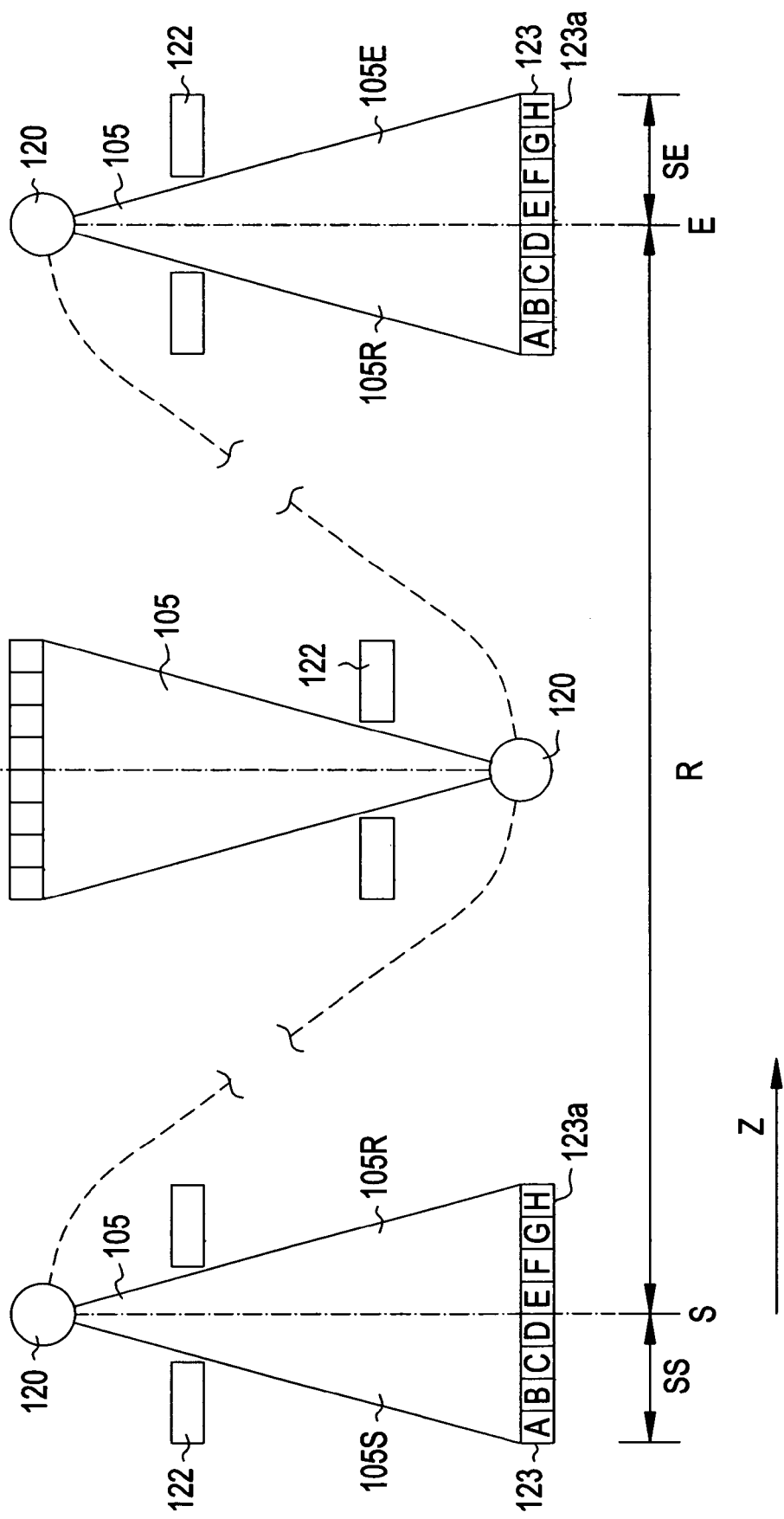

RADIATION TOMOGRAPHY APPARATUS

CROSS REFERENCE TO RELATED APPLICATIONS

This application claims the benefit of Japanese Application No. 2003-317093 filed Sep. 9, 2003.

BACKGROUND OF THE INVENTION

The present invention relates to a radiation tomography apparatus. More specifically, the present invention relates to a radiation tomography apparatus for generating multislice tomographic images.

There is known an X-ray CT (Computed Tomography) apparatus as a radiation tomography apparatus to generate sectional images of an imaging object using radiations such as X-ray. The X-ray CT apparatus is applied to human bodies and solid bodies as imaging objects and is used for a wide range of purposes including medical and industrial purposes.

The X-ray CT apparatus scans around an imaging object using its body axis direction as an axis and irradiates X-ray to the imaging object from an X-ray tube. A collimator shields to shape the X-ray irradiated from the X-ray tube and adjusts an irradiation range of the X-ray so that the X-ray is irradiated to an imaging area of the imaging object. An X-ray detection element of an X-ray detection array detects the X-ray penetrating the imaging object via the collimator. Based on detection data according to the detected X-ray, the X-ray CT apparatus generates a tomographic image for the imaging area of the imaging object.

The X-ray CT apparatus is subject to diversification with respect to locations of imaging objects and purposes of imaging. The X-ray CT apparatus needs to improve image quality such as resolutions and speed up imaging. To satisfy these demands, the X-ray CT apparatus is provided with an X-ray detection array. The X-ray detection array comprises a plurality of X-ray detection elements for X-ray detection that are disposed in an array form along a channel direction and a body axis direction. Available X-ray scanning systems include helical scanning and axial scanning. The axial scanning system irradiates X-ray around an imaging object for each section of an imaging area for the imaging object. The helical scanning system irradiates X-ray around the imaging object helically along the body axis direction.

FIG. 11 illustrates how an X-ray CT apparatus performs a scan according to the helical scanning system. The X-ray CT apparatus is provided with an X-ray detection array 123 comprising a plurality of X-ray detection elements 123a in an array form along the channel direction x and the body axis direction z. In FIG. 11, a plurality of X-ray detection elements 123a is disposed along the channel direction. The X-ray detection elements 123a comprise eight columns from A to H along the body axis direction z. In FIG. 11, FIG. 11(A) shows the start of scanning. FIG 11(B) shows scanning in process. FIG. 11(C) shows the end of scanning. As shown in FIG. 11, the helical scanning system irradiates X-ray around an imaging object helically along the body axis direction z.

As shown in FIG. 11 (A), the scan starts by aligning the irradiation center of an X-ray tube 120 and the center of the X-ray detection array 123 along the body axis direction with one end S of an imaging area R on an imaging object. At this time, the collimator 122 shapes an X-ray 105 from the X-ray tube 120 so that the X-ray forms a pyramid which is symmetrical about the irradiation center and has a specified thickness along the body axis direction z. The X-ray detection array 123 detects the X-ray 105 penetrating the imaging object via the collimator 122 using the X-ray detection elements 123a from columns E to H corresponding to the imaging area R of the imaging object.

During scanning as shown in FIG. 11(B), the X-ray tube 120 helically scans around the imaging object. For example, the X-ray tube 120 irradiates the pyramidal X-ray 105 symmetrical about the irradiation center from a direction opposite to the irradiation direction at the start of scanning. All columns from A to H of the X-ray detection elements 123a detect the X-ray 105 penetrating the imaging object via the collimator 122.

At the end of scanning as shown in FIG. 11 (C), the X-ray tube 120 helically scans around the imaging object. The X-ray tube 120 irradiates the pyramidal X-ray 105 symmetrical about the irradiation center from a direction similar to the irradiation direction at the start of scanning. The X-ray detection array 123 detects the X-ray 105 penetrating the imaging object via the collimator 122, using the X-ray detection elements 123a from columns A to D corresponding to the imaging area R on the imaging object. The scan ends by aligning the center of the X-ray detection array 123 along the body axis direction and the irradiation center of an X-ray tube 120 with the other end E of the imaging area R on the imaging object.

As mentioned above, an X-ray 105R is detected to generate a tomographic image at the start and the end of scanning. This is because the X-ray 105R corresponds to an area belonging to the imaging area R on the imaging object. However, X-rays 105S and 105E are not detected because they correspond to areas SS and SE outside the imaging area R and are not used for tomographic image generation. That is, at the start and the end of scanning, the X-rays 105S and 105E of the X-ray 105 irradiated from the X-ray tube 120 are incident outside the imaging area R from the center of the X-ray detection array 123. Consequently, the X-rays 105S and 105E are not used, and the X-ray 105 irradiated to the imaging object is not used efficiently.

Conventionally, various methods have been proposed to shield the X-rays 105S and 105E that belong to the X-ray 105 irradiated from the X-ray tube 102 and are incident opposite to the imaging area R of the center of the X-ray detection array 123 (e.g., see JP-A No. 234197/1997).

However, the conventional system uses the pyramidal X-ray 105 spreading along the body axis direction z in order to generate a tomographic image having a specified slice thickness. The system not only directly detects the X-ray through the imaging object from the X-ray tube 120, but also detects X-rays as scattered radiations resulting when the original X-ray penetrates the imaging object. This caused to decrease the tomographic image contrast and to generate an artifact. In particular, increasing a pyramid angle of the pyramidal X-ray causes many scattered radiations on the imaging object. For example, the imaging object's abdomen easily causes artifact due to ribs. Not only the helical scanning system, but also the axial scanning system has been subject to this problem.

SUMMARY OF THE INVENTION

It is therefore an object of the present invention to provide a radiation tomography apparatus capable of improving the tomographic image quality and efficiently using radiations such as X-rays by preventing the tomographic image contrast from degrading and preventing artifact from occurring even if many scattered radiations occur.

In order to achieve the above-mentioned objects, a radiation tomography apparatus according to the present invention comprises: radiation irradiation means for scanning around the imaging object and irradiating a radiation to an imaging area of the imaging object with a body axis direction of an imaging object as an axis; a radiation detection array which has radiation detection elements arranged in an array for detecting the radiation penetrating the imaging object and generates detection data according to the radiation detected by the radiation detection elements; irradiation range adjustment means which is disposed between the radiation irradiation means and the radiation detection array and shields the radiation to adjust its irradiation range so that the radiation from the radiation irradiation means is not irradiated to a specified area on the radiation detection array; and tomographic image generation means for generating a tomographic image of an imaging area on the imaging object based on the detection data, wherein the radiation detection array obtains the detection data comprising first and second detection data, in which the first detection data results from the radiation detected by the radiation detection element corresponding to an area not shielded by the irradiation range adjustment means, and the second data results from the radiation detected by the radiation detection element corresponding to an area shielded by the irradiation range adjustment means.

In the above-mentioned radiation tomography apparatus according to the present invention, the radiation irradiation means uses a body axis direction of an imaging object as an axis, scans around the imaging object, and irradiates a radiation to an imaging area of the imaging object. The radiation detection array has radiation detection elements arranged in an array for detecting the radiation penetrating the imaging object and generates detection data according to the radiation detected by the radiation detection elements. The irradiation range adjustment means is disposed between the radiation irradiation means and the radiation detection array and shields the radiation to adjust its irradiation range so that the radiation from the radiation irradiation means is not irradiated to a specified area on the radiation detection array. Here, the radiation detection array obtains the detection data comprising first and second detection data, in which the first detection data results from the radiation detected by the radiation detection element corresponding to an area not shielded by the irradiation range adjustment means, and the second data results from the radiation detected by the radiation detection element corresponding to an area shielded by the irradiation range adjustment means. The tomographic image generation means generates a tomographic image of an imaging area on the imaging object based on the detection data.

According to the present invention, a radiation tomography apparatus is provided which is capable of improving the tomographic image quality and efficiently using radiations such as X-rays, by preventing the tomographic image contrast from degrading and preventing artifact from occurring even if many scattered radiations occur.

Further objects and advantages of the present invention will be apparent from the following description of the preferred embodiments of the invention as illustrated in the accompanying drawings.

BRIEF DESCRIPTION OF THE DRAWINGS

FIG. 4 shows correlation among an X-ray tube, a collimator, and the X-ray detection array in the X-ray CT apparatus as the radiation tomography apparatus according to the embodiment of the present invention, in which

FIG. 6 illustrates a helical scanning system in the X-ray CT apparatus as the radiation tomography apparatus according to the embodiment of the present invention.

FIG. 8 illustrates an axial scanning system in the X-ray CT apparatus as the radiation tomography apparatus according to the embodiment of the present invention.

FIG. 10 shows detection data obtained in accordance with the states in FIGS. 8(C) and 8(D) by the X-ray detection array comprising elements arranged in an array along the channel direction and the body axis direction in the X-ray CT apparatus as the radiation tomography apparatus according to the embodiment of the present invention.

FIG. 11 shows how a conventional X-ray CT apparatus performs scanning according to the helical scanning system.

DETAILED DESCRIPTION OF THE INVENTION

Embodiments of the present invention will be described in further detail with reference to the accompanying drawings.

Figure 1:
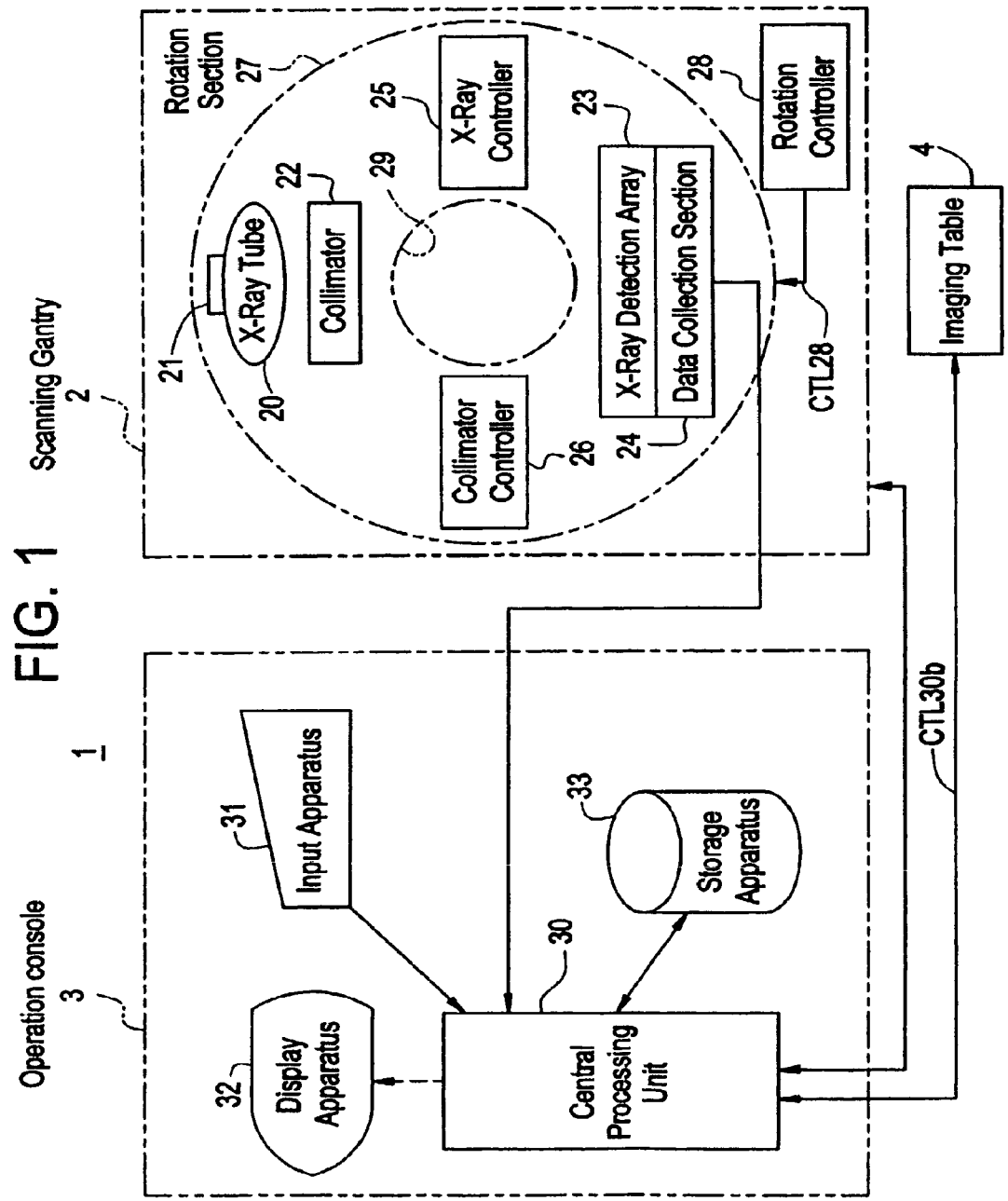
FIG. 1 is a block diagram showing an X-ray CT apparatus as a radiation tomography apparatus according to an embodiment of the present invention.
Figure 2:
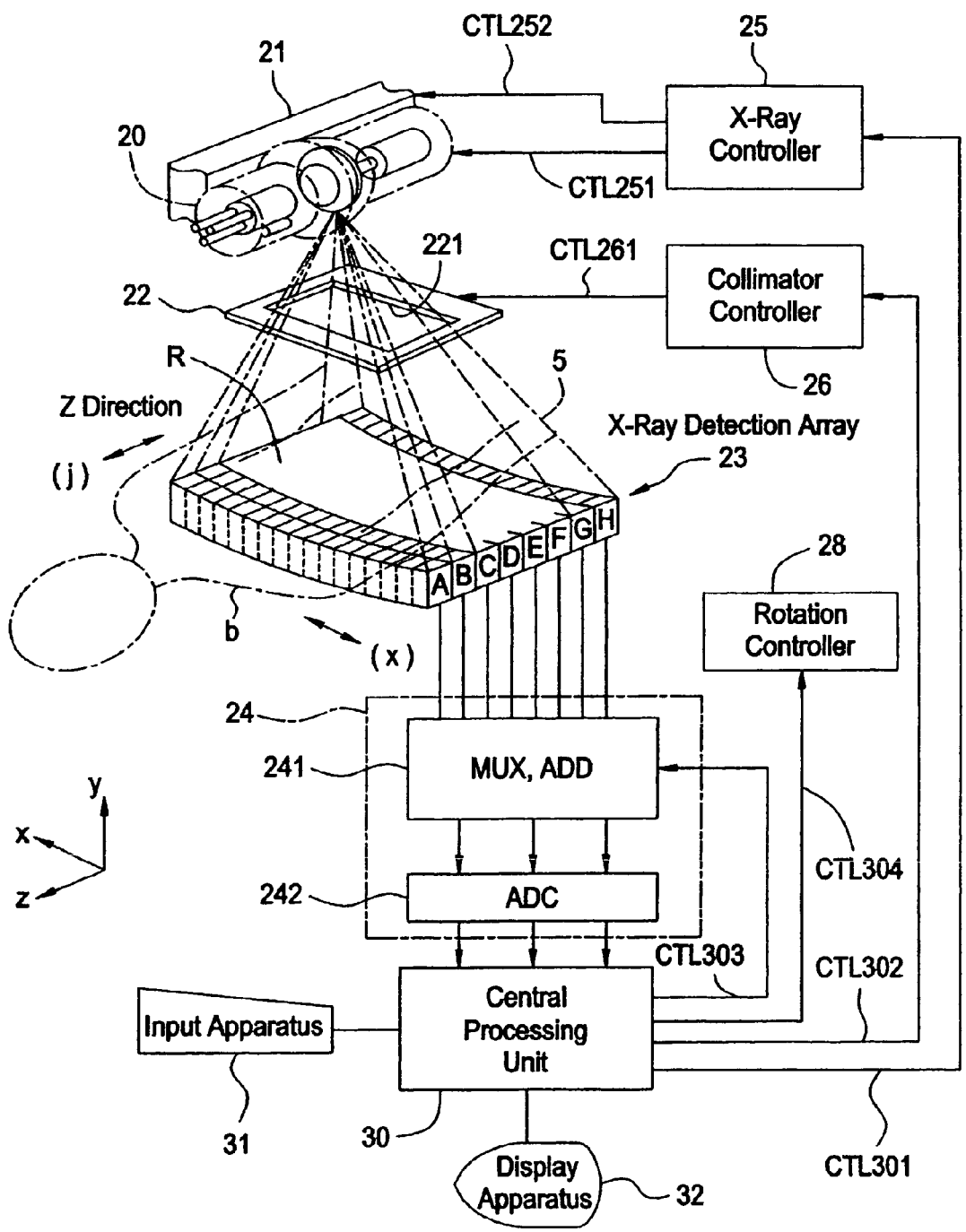
FIG. 2 is a schematic diagram showing main parts of the X-ray CT apparatus as the radiation tomography apparatus according to the embodiment of the present invention.

FIG. 1 is a block diagram showing an overall configuration of an X-ray CT apparatus 1 as a radiation tomography apparatus according to an embodiment of the present invention. FIG. 2 schematically shows major parts of the X-ray CT apparatus 1 as a radiation tomography apparatus according to the embodiment of the present invention.

As shown in FIG. 1, the X-ray CT apparatus 1 according to the embodiment comprises a scanning gantry 2, an operation console 3, and an imaging table 4.

The scanning gantry 2 mainly comprises an X-ray tube 20, an X-ray tube moving section 21, a collimator 22, an X-ray detection array 23, a data collection section 24, an X-ray controller 25, a collimator controller 26, a rotation section 27, and a rotation controller 28. The X-ray tube 20 provides radiation irradiation means according to the present invention. The collimator 22 provides irradiation range adjustment means according to the present invention. The X-ray detection array 23 provides a radiation detection array according to the present invention.

Based on a control signal CTL 251 from the X-ray controller 25, the X-ray tube 20 irradiates an X-ray 5 with a specified intensity through the collimator 22 onto the imaging area R on an imaging object 6.

Based on a control signal CTL 252 from the X-ray controller 25, the X-ray tube moving section 21 moves the irradiation center of the X-ray tube 20 along a body axis direction of the imaging object 6 placed on the imaging table 4 in an X-ray irradiation space 29 of the scanning gantry 2. The body axis direction corresponds to a direction orthogonal to the horizontal of FIG. 1 and a z direction in FIG. 2.

The collimator 22 is disposed between the X-ray tube 20 and the X-ray detection array 23. Based on a control signal CTL 261 from the collimator controller 26, the collimator 22 shields the X-ray 5 irradiated from the X-ray tube 20 in the channel direction and the body axis direction. In this manner, the collimator 22 shapes the pyramidal X-ray 5 having specified widths in the channel direction and the body axis direction to adjust the irradiation range of the X-ray 5. The irradiation range of the X-ray 5 is set by adjusting an aperture opening of the collimator 22 based on the control signal CTL 261. The aperture opening of the collimator 22 is adjusted, for example, by independently moving two plates each provided in the channel direction and the body axis direction.

The X-ray detection array 23 has a plurality of X-ray detection elements as radiation detection elements according to the present invention for detecting the X-ray penetrating the imaging object through the collimator 22. The X-ray detection array comprises X-ray detection elements arranged in an array. The X-ray detection elements detect the X-ray to generate detection data.

Figure 3:
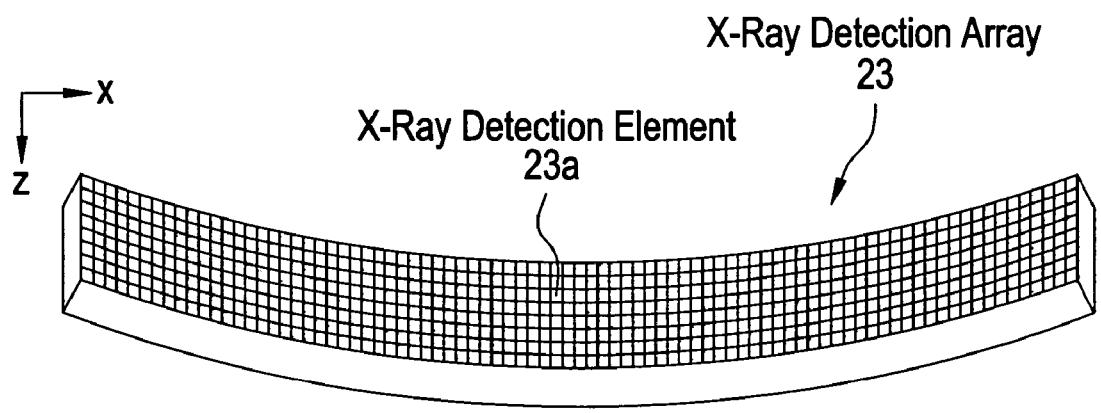
FIG. 3 is a schematic diagram of an X-ray detection array of the X-ray CT apparatus as the radiation tomography apparatus according to the embodiment of the present invention.

FIG. 3 shows a configuration of the X-ray detection array 23 according to the embodiment. As shown in FIG. 3, the X-ray detection array 23 comprises the X-ray detection elements 23*a* arranged in an array along the channel direction x and the body axis direction z. A plurality of two-dimensionally arranged X-ray detection elements 23*a* forms a cylindrically and concavely curved plane of X-ray incidence in its entirety. For example, there are 1000 X-ray detection elements 23*a* arranged in the channel direction x. There are eight X-ray detection elements 23*a* arranged in the body axis direction z. In FIG. 2, these elements along the body axis direction z are represented by symbols A through H.

For example, the X-ray detection element 23*a* is configured by combining a scintillator and a photo diode, but is not limited thereto. For example, there may be provided a semiconductor X-ray detection element using Cadmium Telluride (CdTe) and the like, or an ion chamber X-ray detection element using xenon (Xe) gas.

Figure 4A:
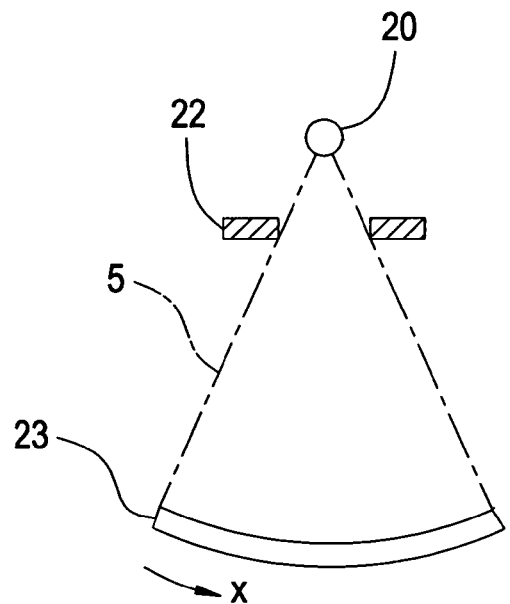
FIG. 4(a) shows a state viewed from a side using a body axis direction as a line of vision.
Figure 4B:
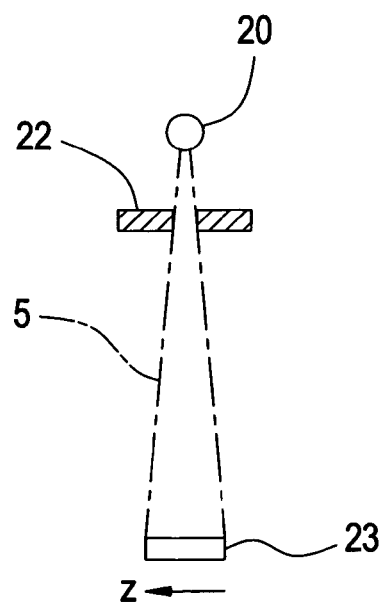
FIG. 4(b) shows a state viewed from a side using a channel direction as a line of vision.
Figure 5:
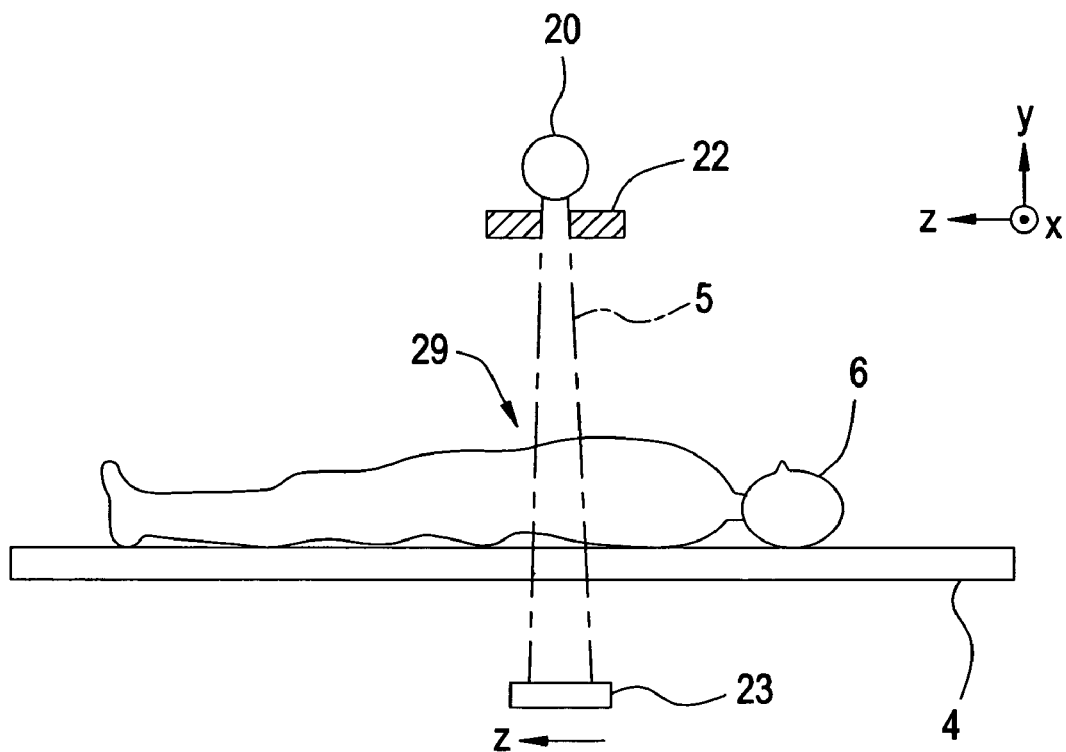
FIG. 5 shows correlation among the X-ray tube, the collimator, and the X-ray detection array in the X-ray CT apparatus as the radiation tomography apparatus according to the embodiment of the present invention, illustrating how an imaging object is scanned in a state viewed from a side using the channel direction as a line of vision.

FIGS. 4 and 5 show correlation among the X-ray tube 20, the collimator 22, and the X-ray detection array 23. In FIG. 4, FIG. 4(*a*) shows a state viewed from a side using the body axis direction z as a line of vision. FIG. 4(*b*) shows a state viewed from a side using the channel direction x as a line of vision. Like FIG. 4(*b*), FIG. 5 shows how the imaging object 6 is imaged in a state viewed from the side using the channel direction x as a line of vision.

As shown in FIGS. 4(*a*) and 4(*b*), the X-ray 5 irradiated from the X-ray tube 20 is shaped by the collimator 22 to be a pyramid having a specified pyramid angle. The shaped X-ray is irradiated to a specified area on the X-ray detection array 23. To scan the imaging object 6 as shown in FIG. 5, the imaging object 6 placed on the imaging table 4 is carried in the X-ray irradiation space 29. The circumference of the imaging object 6 is scanned around an axis, i.e., the body axis direction of the imaging object 6. The X-ray tube 20 irradiates the X-ray 5 onto the imaging area R of the imaging object 6.

The X-ray 5 irradiated from the X-ray tube 20 passes the collimator 22, penetrates the imaging object 6, and then is detected by the X-ray detection array 23. The X-ray detection array 23 according to the embodiment generates first and second detection data. The first detection data is obtained by the X-ray detection elements 23*a* corresponding to an area not shielded by the collimator 22. The second detection data is obtained by the X-ray detection elements 23*a* corresponding to an area shielded by the collimator 22. The first detection data is detected by the X-ray detection elements 23*a* corresponding to the area not shielded by the collimator 22. Therefore, the first detection data is generated by: the X-ray 5 directly irradiated to the X-ray detection elements 23*a* from the X-ray tube 20 through the imaging object 6; and the X-ray 5 as a scattered radiation from the X-ray tube 20 through the imaging object 6. The second detection data is detected by the X-ray detection elements 23*a* corresponding to the area shielded by the collimator 22. Therefore, the second detection data is generated by the X-ray 5 indirectly irradiated to the X-ray detection elements 23*a* from the X-ray tube 20 through the imaging object 6. That is, the second detection data is generated from the X-ray 5 that is irradiated from the X-ray tube 20, penetrates the imaging object 6, and becomes a scattered radiation.

The data collection section 24 collects detection data from the respective X-ray detection elements 23*a* of the X-ray detection array 23 and outputs the collected detection data to the operation console 3. As shown in FIG. 2, the data collection section 24 has a selection/addition switching circuit (MUX,ADD) 241 and an analog/digital converter (ADC 242). The selection/addition switching circuit 241 selects detection data detected by the X-ray detection elements 23*a* of the X-ray detection array 23 according to a control signal CTL 303 from a central processing unit 30 in the operation console 3. Alternatively, the selection/addition switching circuit 241 adds detection data to each other by changing combinations and outputs a result to the analog/digital converter 242. After the selection/addition switching circuit 241 selects or adds detection data to each other in any combination, the analog/digital converter 242 converts the detection data from an analog signal into a digital signal and outputs the digital signal to the central processing unit 30 in the operation console 3.

In accordance with a control signal CTL 301 from the central processing unit 30 in the operation console 3, the X-ray controller 25 outputs the control signal CTL 251 to the X-ray tube 20 for controlling the X-ray irradiation. Further, in accordance with the control signal CTL 301 from the central processing unit 30 in the operation console 3, the X-ray controller 25 outputs the control signal CTL 252 to an X-ray tube moving section 21. In this manner, the X-ray controller 25 moves the irradiation center of the X-ray tube 20 in the body axis direction z for a distance corresponding to a signal command.

In accordance with a control signal CTL 302 from the central processing unit 30 in the operation console 3, the collimator controller 26 outputs the control signal CTL 261 to the collimator 22. In this manner, the collimator controller 26 adjusts the opening of an aperture 221 of the collimator 22 to shape the X-ray 5 irradiated from the X-ray tube 20. The shaped X-ray 5 is irradiated to a targeted area on the X-ray detection array 23.

The rotation section 27 rotates in a specified direction based on a control signal CTL 28 from the rotation controller 28. The rotation section 27 is mounted with the X-ray tube 20, the X-ray tube moving section 21, the collimator 22, the X-ray detection array 23, the data collection section 24, the X-ray controller 25, and the collimator controller 26. As the rotation section 27 rotates, the constituent elements change the positional relation with reference to the imaging object 6 carried in the X-ray irradiation space 29. Rotating the rotation section 27 collects the detection data by irradiating the X-ray 5 from a plurality of view directions around the body axis direction of the imaging object 6.

In accordance with a control signal CTL 304 from the central processing unit 30 in the operation console 3, the rotation controller 28 outputs the control signal CTL 28 to rotation section 27 to rotate it for the specified number of rotations in a specified direction.

The operation console 3 mainly comprises the central processing unit 30 having tomographic image generation means according to the present invention, an input apparatus 31, a display apparatus 32, and a storage apparatus 33.

For example, the central processing unit 30 comprises a microcomputer and the like, and outputs a control signal CTL 30b to the imaging table 4. This control signal is used to carry the imaging table 4 in or out of the X-ray irradiation space 29 for the scanning gantry 2. Here, the imaging table 4 is used to place the imaging object 6 in accordance with a command entered from the input apparatus 31.

When the input apparatus 31 inputs a command to start multislice scanning, the central processing unit 30 receives this command and outputs the control signal CTL 304 to the rotation controller 28 of the scanning gantry 2 in order to rotate the rotation section 27 in a specified direction for the specified number of rotations according to the command. As mentioned above, the rotation section 27 is mounted with the X-ray tube 20, the X-ray tube moving section 21, the collimator 22, the X-ray detection array 23, the data collection section 24, the X-ray controller 25, and the collimator controller 26 for the scanning gantry 2. The central processing unit 30 then outputs the control signal CTL 301 to the X-ray controller 25 to allow the X-ray tube 20 of the scanning gantry 2 to irradiate the X-ray 5.

When the input apparatus 31 inputs information about the imaging area R on the imaging object 6, the central processing unit 30 receives this information and outputs the control signal CTL 301 to the X-ray controller 25 in order to move the irradiation center of the X-ray tube 20 in the body axis direction z for a distance corresponding to the command. The central processing unit 30 further outputs the control signal CTL 302 to the collimator controller 26 to allow the collimator 22 to irradiate the X-ray 5 with a specified opening.

Further, when the input apparatus 31 inputs information about the imaging area R on the imaging object 6, the central processing unit 30 responds to this information and outputs the control signal CTL 303 to the selection/addition switching circuit 241 of the data collection section 24 in order to dynamically select detection data detected by the X-ray detection elements of the X-ray detection array 23 or to add the detection signals to each other by changing combinations. For example, it is possible to organize detection data for eight columns from A to H corresponding to the X-ray detection elements into four pieces of data by combining two columns such as columns A and B, C and D, E and F, and G and H. The four pieces of data are then supplied to the analog/digital converter 242.

In addition, the central processing unit 30 functions as tomographic image generation means. The central processing unit 30 reconstructs an image based on detection data collected in the data collection section 24 from a plurality of view directions and generates a plurality of tomographic images. For example, the central processing unit 30 uses filtered back projection for the image reconstruction. The central processing unit 30 then allows the display apparatus 32 to display the reconstructed image.

The input apparatus 31 is provided to supply information such as imaging conditions to the central processing unit 30. The input apparatus 31 comprises a keyboard, a mouse, and the like. The input apparatus 31 may be connected to the scanning gantry 2 or the imaging table 4.

The display apparatus 32 displays reconstructed images and the other types of information based on commands from the central processing unit 30.

The storage apparatus 33 stores various data, reconstructed images, programs, and the like. The central processing unit 30 accesses stored data as needed.

The following describes operations of the above-mentioned X-ray CT apparatus 1 as the radiation tomography apparatus according to the embodiment.

FIG. 6 illustrates a helical scanning system using the above-mentioned X-ray CT apparatus 1 according to the embodiment. The X-ray CT apparatus 1 rotates to helically scan around the imaging object 6 along the body axis direction z from one end S to the other end E of the imaging area R on the imaging object 6. FIG. 6(A) shows the start of scanning. FIG. 6(B) shows scanning in process. FIG. 6(C) shows the end of scanning.

Figures 7A, 7B, 7C:
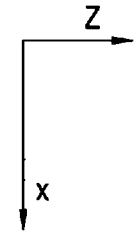
FIG. 7 shows detection data obtained in accordance with FIG. 6 by the X-ray detection array comprising elements arranged in an array along the channel direction and the body axis direction in the X-ray CT apparatus as the radiation tomography apparatus according to the embodiment of the present invention.

FIG. 7 shows detection data obtained in accordance with FIG. 6 by the X-ray detection array 23 comprising elements arranged in an array along the channel direction x and the body axis direction z. FIG. 7 assumes the X-ray detection array 23 comprising eight X-ray detection elements 23a each along the channel direction x and the body axis direction z. The X-ray detection elements 23a are sequentially assigned with numbers 1 to 8 as address positions along the channel direction x. The X-ray detection elements 23a are sequentially assigned with letters A to H as address positions along the body axis direction z. In FIG. 7, boxed positions correspond to the second detection data to be obtained. The other positions (not boxed) correspond to the first detection data to be obtained. FIG. 7(A) shows the start of scanning. FIG. 7(B) shows scanning in process. FIG. 7(C) shows the end of scanning.

In the helical scanning system, prior to scanning of the X-ray 5, an operator first uses the input apparatus 31 to supply the central processing unit 30 with information about the imaging area R on the imaging object 6. Based on the information supplied from the input apparatus 31, the central processing unit 30 outputs the control signal CTL 30b to the imaging table 4 in order to carry the imaging table 4 for placing the imaging object 6 in or out of the X-ray irradiation space 29 of the scanning gantry 2. The imaging table 4 is positioned so that the imaging area R of the imaging object 6 is aligned with a desired position in the X-ray irradiation space 29 of the scanning gantry 2. The central processing unit 30 outputs the control signal CTL 301 to the X-ray controller 25. This signal allows the X-ray controller 25 to output the control signal CTL 251 to the X-ray tube 20. The X-ray tube 20 then irradiates the X-ray 5. Further, the central processing unit 30 outputs the control signal CTL 302 to the collimator controller 26. This signal allows the collimator controller 26 to supply the collimator 22 with the control signal CTL 261 that controls the opening of the aperture 221 of the collimator 22.

At the start of scanning as shown in FIG. 6(A), the center of the X-ray detection array 23 along the body axis direction z aligns with one end S of the imaging area R on the imaging object 6 along the body axis direction z. That is, the X-ray detection array 23 is aligned so that one end S of the imaging area R on the imaging object 6 is positioned near the boundary between the columns D and E in the X-ray detection elements 23*a*.

At the start of helical scanning, the collimator controller 26 controls the collimator 22 as follows. Under this control, the collimator 22 shields X-ray 5 incident on an area SS opposite to the imaging area R from the center of the X-ray detection array 23 along the body axis direction z. That is, the collimator controller 26 controls the collimator 22 so as to directly irradiate the X-ray 5 to columns E, F, G, and H and not to columns A, B, C, and D of the X-ray detection elements 23*a* arranged in the body axis direction of the X-ray detection array 23.

The X-ray detection array 23 generates the first and second detection data. The first detection data is obtained by the X-ray detection elements 23*a* corresponding to the area not shielded by the collimator 22. The second detection data is obtained by the X-ray detection elements 23*a* corresponding to the area shielded by the collimator 22. As shown in FIG. 7(A), the X-ray detection array 23 generates the first detection data S51 to S58, S61 to S68, S71 to S78, and S81 to S88 from the columns E, F, G, and H. The X-ray detection array 23 generates the second detection data S11 to S18, S21 to S28, S31 to S38, and S41 to S48 by scattered radiation from columns A, B, C, and D.

The central processing unit 30 outputs the control signal CTL 303 to the selection/addition switching circuit 241 to collect the detection data obtained by the X-ray detection array 23. That is to say, the first detection data S51 to S58, S61 to S68, S71 to S78, and S81 to S88 are collected from the columns E, F, G, and H. The second detection data S11 to S18, S21 to S28, S31 to S38, and S41 to S48 are collected from columns A, B, C, and D. After the selection/addition switching circuit 241 collects the detection data in an analog signal, the analog/digital converter 242 converts this signal into a digital signal and outputs it to the central processing unit 30.

During the helical scanning as shown in FIG. 6(B), the X-ray tube 20 helically scans around the imaging object 6. The X-ray tube 20 irradiates the pyramidal X-ray 5 symmetrical about the irradiation center from a direction opposite to the irradiation direction at the start of scanning.

The collimator controller 26 controls the collimator 22 to widen the range of irradiating the X-ray 5 compared to the range at the start of scanning while the scan progresses from the one end S to the other end E of the imaging area R on the imaging object 6 along the body axis direction z. For example, the collimator 22 is controlled as follows. At the start of scanning, the X-ray 5 is directly irradiated to columns E through H in the X-ray detection elements 23*a* of the X-ray detection array 23 along the body axis direction. During scanning, the irradiation range gradually widens on the X-ray detection elements 23*a* arranged along the body axis direction in the X-ray detection array 23. The X-ray 5 is directly irradiated on all columns A through H of the X-ray detection elements 23*a* arranged along the body axis direction in the X-ray detection array 23.

As shown in FIG. 7(B), the X-ray detection array 23 obtains detection data, i.e., the first detection data M11 to M18, M21 to M28, M31 to M38, M41 to M48, M51 to M58, M61 to M68, M71 to M78, and M81 to M88 from all columns A to H arranged in the X-ray detection array 23 along the body axis direction. The central processing unit 30 outputs the control signal CTL 303 to the selection/addition switching circuit 241 to collect the first detection data as detection data obtained by the X-ray detection array 23 from columns A to H. That is, the first detection data includes M11 to M18, M21 to M28, M31 to M38, M41 to M48, M51 to M58, M61 to M68, M71 to M78, and M81 to M88. After the selection/addition switching circuit 241 collects the detection data in an analog signal, the analog/digital converter 242 converts this signal into a digital signal and outputs it to the central processing unit 30.

At the end of helical scanning as shown in FIG. 6(C), the X-ray tube 20 helically scans around the imaging object 6. The X-ray tube 20 irradiates the pyramidal X-ray 5 symmetrical about the irradiation center from the same direction as for the start of scanning. The scan terminates by aligning the center of the X-ray detection array 23 along the body axis direction with the other end E of the imaging area R on the imaging object 6.

As the scan progresses from the one end S to the other end E of the imaging area R on the imaging object 6 along the body axis direction z, the collimator controller 26 controls the collimator 22 so that the range of irradiating the X-ray 5 becomes wider during scanning than at the end of scanning. That is to say, the control is provided to make the irradiation range of the X-ray 5 narrower at the end of scanning than during scanning. At the end of scanning, for example, the collimator 22 is controlled to gradually narrow the range of irradiation on the X-ray detection elements 23*a* arranged in the X-ray detection array 23 along the body axis direction compared to the scanning in progress. Further, the collimator 22 is controlled to shield the X-ray 5 incident on an area SE opposite to the imaging area R from the center of the X-ray detection array 23 along the body axis direction z. That is to say, the collimator controller 26 controls the collimator 22 at the end of scanning so as to directly irradiate the X-ray 5 to columns A, B, C, and D and not to columns E, F, G, and H of the X-ray detection elements 23*a* comprising columns A through H arranged in the body axis direction of the X-ray detection array 23.

The X-ray detection array 23 generates the first and second detection data at the end of scanning. The first detection data is obtained by the X-ray detection elements 23*a* corresponding to the area not shielded by the collimator 22. The second detection data is obtained by the X-ray detection elements 23*a* corresponding to the area shielded by the collimator 22. As shown in FIG. 7(C), the X-ray detection array 23 generates the first detection data E11 to E18, E21 to E28, E31 to E38, and E41 to E48 from columns A, B, C, and D. The X-ray detection array 23 generates the second detection data E51 to E58, E61 to E68, E71 to E78, and E81 to E88 from the columns E, F, G, and H.

The central processing unit 30 outputs the control signal CTL 303 to the selection/addition switching circuit 241 to collect the detection data obtained by the X-ray detection array 23. That is to say, the first detection data are collected from the columns A, B, C, and D. The second detection data E51 to E58, E61 to E68, E71 to E78, and E81 to E88 are collected from columns E, F, G, and H. After the selection/addition switching circuit 241 collects the detection data in an analog signal, the analog/digital converter 242 converts this signal into a digital signal and outputs it to the central processing unit 30.

At the end of scanning, the central processing unit 30 functions as the tomographic image generation means. The central processing unit 30 reconstructs an image based on detection data collected in the data collection section 24 from a plurality of view directions and generates a plurality of tomographic images. For example, the central processing unit 30 uses filtered back projection for the image reconstruction.

Prior to the image reconstruction, the central processing unit 30 as the tomographic image generation means corrects the first detection data using the second detection data.

The central processing unit 30 as the tomographic image generation means corrects the first detection data obtained at the start of scanning using the second detection data obtained at the start of scanning as shown in FIG. 7(A). To do this, for example, suppose that the first and second detection data are obtained by the X-ray detection elements arranged in the X-ray detection array corresponding to the positions along the channel direction. The system first calculates an average value of the second detection data obtained correspondingly to the positions in the X-ray detection array along the channel direction. The first detection data is obtained correspondingly to the same positions along the channel direction as for the second detection data, i.e., original data of the average value. The system calculates difference data between each of the first detection data and the average value of the corresponding second detection data. The system corrects the first detection data by replacing it with the difference data. Specifically, there are a plurality of second detection data S11 to S18, S21 to S28, S31 to S38, and S41 to S48 obtained at columns A to D and a plurality of first detection data S51 to S58, S61 to S68, S71 to S78, and S81 to S88 obtained at columns E to H. At the start of scanning, the system first calculates an average value of the second detection data S11, S21, S31, and S41 arranged at address 1 along the channel direction x, for example. The first detection data S51, S61, S71, and S81 are arranged at address 1 along the channel direction x. The system calculates a difference between each of the first detection data and the average value of the second detection data S11, S21, S31, and S41 to correct the first detection data S51, S61, S71, and S81. The difference data is used as detection data for image reconstruction. The system also performs the above-mentioned correction at addresses 2 through 8 along the channel direction x.

The central processing unit 30 as the tomographic image generation means corrects the first detection data obtained at the end of scanning by using the second detection data obtained at the end of scanning as shown in FIG. 7(C). To do this, for example, suppose that the first and second detection data are obtained by the X-ray detection elements arranged in the X-ray detection array corresponding to the positions along the channel direction. The system first calculates an average value of the second detection data obtained correspondingly to the positions in the X-ray detection array along the channel direction. The first detection data is obtained correspondingly to the same positions along the channel direction as for the second detection data, i.e., original data of the average value. The system calculates difference data between each of the first detection data and the average value of the corresponding second detection data. The system corrects the first detection data by replacing it with the difference data. Specifically, there are a plurality of first detection data E11 to E18, E21 to E28, E31 to E38, E41 to E48 obtained at columns A to D and a plurality of second detection data E51 to E58, E61 to E68, E71 to E78, E81 to E88 obtained at columns E to H. At the end of scanning, the system calculates an average value of the second detection data E51, E61, E71, and E81 arranged at address 1 along the channel direction x, for example. The first detection data E11, E21, E31, and E41 are arranged at address 1 along the channel direction x. The system calculates a difference between each of the first detection data and the average value of the second detection data E51, E61, E71, and E81 to correct the first detection data E11, E21, E31, and E41. The difference data is used as detection data for image reconstruction. The system also performs the above-mentioned correction at addresses 2 through 8 along the channel direction x.

During scanning as shown in FIG. 7(B), the first detection data is corrected in the same manner as for the start and the end of scanning. To do this, the system changes the second detection data used for correcting the first detection data in accordance with the positions of detection data obtained by the X-ray detection elements 23a of the X-ray detection array 23 during scanning. Alternatively, it may be preferable to find a weighted average in accordance with the positions of detection data obtained by the X-ray detection elements 23a of the X-ray detection array 23 during scanning.

Firstly, the first detection data is obtained correspondingly to part of the imaging area R on the imaging object 6 from one end S to the center M along the body axis direction z. In this case, the system corrects the first detection data using the second detection data obtained at the beginning of scanning. Secondly, the first detection data is obtained correspondingly to the remaining part of the imaging area R on the imaging object 6 from the other end E to the center M along the body axis direction z. In this case, the system corrects the first detection data using the second detection data obtained at the beginning of scanning.

The central processing unit 30 reconstructs the image based on the corrected first detection data, then allows the display apparatus 32 to display the reconstructed image.

FIG. 8 illustrates an axial scanning system using the X-ray CT apparatus according to the embodiment. The axial scanning system rotates to scan around the imaging object 6 on a section basis in the imaging area R from one end S to the other end E of the imaging area R on the imaging object 6 along the body axis direction z. Here, FIGS. 8(A) and 8(B) show operations at one end S, i.e., a position to start scanning. FIG. 8(A) shows a state before scanning. FIG. 8(B) shows the start of scanning at one end S for the first rotation. FIGS. 8(C) and 8(D) show operations at the other end E, i.e., a position to terminate scanning after the scan moves from one end S to the other end E sequentially on a section basis. FIG. 8(C) shows a state when the scan terminates at the other end E. FIG. 8(D) shows a state after scanning.

Figures 9A, 9B:
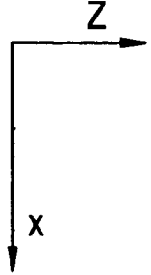
FIG. 9 shows detection data obtained in accordance with the states in FIGS. 8(A) and 8(B) by the X-ray detection array comprising elements arranged in an array along the channel direction and the body axis direction in the X-ray CT apparatus as the radiation tomography apparatus according to the embodiment of the present invention.

FIGS. 9 and 10 show detection data obtained in accordance with the states in FIG. 8 by the X-ray detection array 23 comprising elements arranged in an array along the channel direction x and the body axis direction z. FIGS. 9 and 10 assume the X-ray detection array 23 comprising eight X-ray detection elements 23a each along the channel direction x and the body axis direction z. The X-ray detection elements 23a are sequentially assigned with numbers 1 to 8 as address positions along the channel direction x. The X-ray detection elements 23a are sequentially assigned with letters A to H as address positions along the body axis direction z. In FIGS. 9 and 10, boxed positions correspond to the second detection data to be obtained. The other positions (not boxed) correspond to the first detection data to be obtained. FIGS. 9(A) and 9(B) correspond to FIGS. 8(A) and 8(B), respectively. FIG. 9(A) shows the data before scanning. FIG. 9(B) shows the data when the scan starts at one end S. FIG. 10 shows detection data at the other end E, i.e., the position to terminate scanning after the scan moves from one end S to the other end E sequentially on a section basis. FIGS. 10(A) and 10(B) correspond to FIGS. 8(C) and 8(D), respectively. FIG. 10(A) shows the data at the end of scanning. FIG. 10(B) shows the data after scanning.

Prior to scanning of the X-ray 5 in the axial scanning system, like the above-mentioned helical scanning system, an operator first uses the input apparatus 31 to supply the central processing unit 30 with information about the imaging area R on the imaging object 6. Based on the information supplied from the input apparatus 31, the central processing unit 30 outputs the control signal CTL 30b to the imaging table 4 in order to carry the imaging table 4 for placing the imaging object 6 in or out of the X-ray irradiation space 29 of the scanning gantry 2. The imaging table 4 is positioned so that the imaging area R of the imaging object 6 is aligned with a target position in the X-ray irradiation space 29 of the scanning gantry 2. The central processing unit 30 outputs the control signal CTL 301 to the X-ray controller 25. This signal allows the X-ray controller 25 to output the control signal CTL 251 to the X-ray tube 20. The X-ray tube 20 then irradiates the X-ray 5. Further, the central processing unit 30 outputs the control signal CTL 302 to the collimator controller 26. This signal allows the collimator controller 26 to supply the collimator 22 with the control signal CTL 261 that controls the opening of the aperture 221 of the collimator 22.

Before the start of scanning as shown in FIG. 8(A), the collimator controller 26 controls the collimator 22 near one end S to start scanning so that the X-ray 5 is not irradiated onto specified elements in the X-ray detection array 23. According to the embodiment, before the start of scanning like at the start of scanning (to be described), the collimator 22 is controlled so that one end of the X-ray detection array 23 along the body axis direction z aligns with one end S of the imaging area R on the imaging object 6 along the body axis direction z.

The X-ray tube 20 irradiates the X-ray 5. The X-ray detection array 23 obtains the first detection data using the X-ray detection elements 23a corresponding to an area not shielded by the collimator 22. The X-ray detection array 23 obtains the second detection data using the X-ray detection elements 23a corresponding to an area shielded by the collimator 22. Before scanning as shown in FIG. 9(A), for example, the X-ray 5 is directly irradiated from the X-ray tube 20 to columns C, D, E, and F around the center of the X-ray detection array 23 along the body axis direction. The X-ray detection array 23 uses columns C, D, E, and F to detect the X-ray directly irradiated from the X-ray tube 20 and the indirect X-ray as scattered radiation. In this manner, the X-ray detection array 23 obtains the first detection data S31 to S38, S41 to S48, S51 to S58, and S61 to S68. The collimator 22 shields columns A, B, Q and H at the ends of the X-ray detection array 23 along the body axis direction. The X-ray detection array 23 uses columns A, B, Q and H shielded by the collimator 22 to obtain the second detection data S11 to S18, S21 to S28, S71 to S78, and S81 to S88 generated by the scattered radiation.

The central processing unit 30 outputs the control signal CTL 303 to the selection/addition switching circuit 241 to collect the detection data obtained by the X-ray detection array 23. That is to say, the first detection data S31 to S38, S41 to S48, S51 to S58, and S61 to S68 are collected from the columns C, D, E, and F. The second detection data S81 to S18, S21 to S28, S71 to S78, and S81 to S88 are collected from columns A, B, G, and H. After the selection/addition switching circuit 241 collects the detection data in an analog signal, the analog/digital converter 242 converts this signal into a digital signal and outputs it to the central processing unit 30.

At the start of scanning as shown in FIG. 8(B), one end of the X-ray detection array 23 along the body axis direction z again aligns with one end S of the imaging area R on the imaging object 6 along the body axis direction z. That is to say, the X-ray detection array 23 is positioned so that its end at column A aligns with one end S of the imaging area R on the imaging object 6. By fixing the position along the body axis direction, the system makes one rotation around the imaging object 6 and irradiates the X-ray 5 from a plurality of view directions around the imaging object 6.

Here, the scan takes place from one end S to the other end E of the imaging area R on the imaging object 6 along the body axis direction z. At this time, the collimator controller 26 controls the collimator 22 so as to widen the range of irradiating the X-ray 5 compared to before the start of scanning. At the start of scanning, for example, the collimator 22 is controlled so that the X-ray 5 is directly irradiated to all columns A to H arranged in the X-ray detection array 23 along the body axis direction.

As shown in FIG. 9(B), the X-ray detection array 23 obtains detection data, i.e., the first detection data S'11 to S'18, S'21 to S'28, S'31 to S'38, S'41 to S'48, S'51 to S'58, S'61 to S'68, S'71 to S'78, and S'81 to S'88 from all columns A to H of the X-ray detection elements 23a arranged in the X-ray detection array 23 along the body axis direction. The central processing unit 30 outputs the control signal CTL 303 to the selection/addition switching circuit 241 and collects the first detection data S'11 to S'18, S'21 to S'28, S'31 to S'38, S'41 to S'48, S'51 to S'58, S'61 to S'68, S'71 to S'78, and S'81 to S'88 from columns A to H as detection data obtained by the X-ray detection array 23. After the selection/addition switching circuit 241 collects the detection data in an analog signal, the analog/digital converter 242 converts this signal into a digital signal and outputs it to the central processing unit 30.

Then, as shown in FIG. 8(C), the scan progresses from one end S to the other end E sequentially on a section basis. At the end of scanning, the other end of the X-ray detection array 23 along the body axis direction z aligns with the other end S of the imaging area R on the imaging object 6 along the body axis direction z. That is to say, the X-ray detection array 23 is positioned so that its end at column H aligns with the other end E of the imaging area R on the imaging object 6. By fixing the position along the body axis direction, the system makes one rotation around the imaging object 6 and irradiates the X-ray 5 from a plurality of view directions around the imaging object 6.

Here, the scan takes place from one end S to the other end E of the imaging area R on the imaging object 6 along the body axis direction z. At this time, the collimator controller 26 controls the collimator 22 so as to widen the range of irradiating the X-ray 5 compared to after the start of scanning (to be described). At the start of scanning, for example, the collimator 22 is controlled so that the X-ray 5 is directly irradiated to all columns A to H arranged in the X-ray detection array 23 along the body axis direction.

As shown in FIG. 10(A), the X-ray detection array 23 obtains detection data, i.e., the first detection data E11 to E18, E21 to E28, E31 to E38, E41 to E48, E51 to E58, E61 to E68, E71 to E78, E81 to E88 from all columns A to H of the X-ray detection elements 23a arranged in the X-ray detection array 23 along the body axis direction. The central processing unit 30 outputs the control signal CTL 303 to the selection/addition switching circuit 241 and collects the first detection data E11 to E18, E21 to E28, E31 to E38, E41 to E48, E51 to E58, E61 to E68, E71 to E78, E81 to E88 from columns A to H as detection data obtained by the X-ray detection array 23. After the selection/addition switching circuit 241 collects the detection data in an analog signal, the analog/digital converter 242 converts this signal into a digital signal and outputs it to the central processing unit 30.

At the end of scanning as shown in FIG. 8(D), the collimator controller 26 controls the collimator 22 near the other end E to end scanning so that the X-ray 5 is not irradiated onto specified elements in the X-ray detection array 23. According to the embodiment, after the end of scanning like at the above-mentioned end of scanning, the collimator 22 is controlled so that the other end of the X-ray detection array 23 along the body axis direction z aligns with the other end E of the imaging area R on the imaging object 6 along the body axis direction z.

The X-ray tube 20 irradiates the X-ray 5. The X-ray detection array 23 obtains the first detection data using the X-ray detection elements 23a corresponding to an area not shielded by the collimator 22. The X-ray detection array 23 obtains the second detection data using the X-ray detection elements 23a corresponding to an area shielded by the collimator 22. As shown in FIG. 10(B), for example, the X-ray detection array 23 obtains the first detection data E'31 to E'38, E'41 to E'48, E'51 to E'58, and E'61 to E'68. In this case, near the other end E of the imaging area R on the imaging object 6, the X-ray is directly irradiated to columns C, D, E, and F around the center of the X-ray detection array 23 along the body axis direction. The X-ray detection array 23 obtains the second detection data E'11 to E'18, E'21 to E'28, E'71 to E'78, and E'81 to E'88 generated by the scattered radiation. In this case, the collimator 22 shields columns A, B, G, and H at the ends of the X-ray detection array 23 along the body axis direction.

The central processing unit 30 outputs the control signal CTL 303 to the selection/addition switching circuit 241 to collect the detection data obtained by the X-ray detection array 23. That is to say, the first detection data E'31 to E'38, E'41 to E'48, E'51 to E'58, and E'61 to E'68 are collected from the columns C, D, E, and F. The second detection data E'11 to E'18, E'21 to E'28, E'71 to E'78, and E'81 to E'88 are collected from columns A, B, G, and H. After the selection/addition switching circuit 241 collects the detection data in an analog signal, the analog/digital converter 242 converts this signal into a digital signal and outputs it to the central processing unit 30.

Thereafter, the central processing unit 30 functions as the tomographic image generation means. The central processing unit 30 reconstructs an image based on detection data collected in the data collection section 24 from a plurality of view directions and generates a plurality of tomographic images. For example, the central processing unit 30 uses filtered back projection for the image reconstruction.

Prior to the image reconstruction, the central processing unit 30 as the tomographic image generation means corrects the first detection data using the second detection data in the axial scanning system as well as the above-mentioned helical scanning system.

For example, the central processing unit 30 as the tomographic image generation means corrects the first detection data obtained at the start of scanning using the second detection data obtained before the start of scanning. To do this, for example, suppose that the first and second detection data are obtained by the X-ray detection elements arranged in the X-ray detection array corresponding to the positions along the channel direction. The system first calculates an average value of the second detection data obtained correspondingly to the positions in the X-ray detection array along the channel direction. The first detection data is obtained correspondingly to the same positions along the channel direction as for the second detection data, i.e., original data of the average value. The system calculates difference data between each of the first detection data and the average value of the corresponding second detection data. The system corrects the first detection data by replacing it with the difference data. Specifically, there are a plurality of second detection data S11 to S18, S21 to S28, S71 to S78, and S81 to S88 obtained at columns A, B, G, and H before the start of scanning, and a plurality of first detection data S'11 to S'18, S'21 to S'28, S'31 to S'38, S'41 to S'48, S'51 to S'58, S'61 to S'68, S'71 to S'78, and S'81 to S'88 obtained at columns A to H at the start of scanning. With respect to these data, the system calculates an average value of the second detection data obtained correspondingly to the positions along the channel direction. For example, the system calculates an average value of the second detection data S11, S21, S71, and S81 at address 1 along the channel direction x. At the start of scanning, the first detection data S'11 to S'18 are sequentially obtained at address 1 along the channel direction x. Before the start of scanning, the second detection data S11, S21, S71, and S81 are sequentially obtained at address 1 for the same elements along the channel direction x. In this case, the system calculates difference data between each of the first detection data and the average value of the second detection data to correct the first detection data. The difference data is used as detection data for image reconstruction. The system also performs the above-mentioned correction at addresses 2 through 8 along the channel direction x.

The central processing unit 30 as the tomographic image generation means corrects the first detection data obtained at the end of scanning by using the second detection data obtained after the end of scanning. To do this, for example, suppose that the first and second detection data are obtained by the X-ray detection elements arranged in the X-ray detection array corresponding to the positions along the channel direction. The system calculates an average value of the second detection data obtained correspondingly to the positions in the X-ray detection array along the channel direction. The first detection data is obtained correspondingly to the same positions along the channel direction as for the second detection data, i.e., original data of the average value. The system calculates difference data between each of the first detection data and the average value of the corresponding second detection data. The system corrects the first detection data by replacing it with the difference data. Specifically, there are a plurality of second detection data E'11 to E'18, E'21 to E'28, E'71 to E'78, and E'81 to E'88 obtained at columns A, B, G, and H at the end of scanning and a plurality of first detection data E11 to E18, E21 to E28, E31 to E38, E41 to E48, E51 to E58, E61 to E68, E71 to E78, and E81 to E88 obtained at columns A to H at the end of scanning. With respect to these data, the system calculates an average value of the second detection data obtained correspondingly to the positions along the channel direction. For example, the system calculates an average value of the second detection data E'11, E'21, E'71, and E'81 at address 1 along the channel direction x. At the end of scanning, the first detection data E11 to E18 are sequentially obtained at address 1 along the channel direction x. After the end of scanning, the second detection data E'11, E'21, E'71, and E'81 are sequentially obtained at address 1 for the same elements along the channel direction x. In this case, the system calculates difference data between each of the first detection data and the average value of the second detection data to correct the first detection data. The difference data is used as detection data for image reconstruction. The system also performs the above-mentioned correction at addresses 2 through 8 along the channel direction x.

The system also corrects the first detection data (not shown) during scanning similarly at the start and the end of scanning. In this case, the system changes the second detection data used for correcting the first detection data in accordance with positions of the X-ray detection elements 23a of the X-ray detection array 23. For example, the system similarly corrects the first detection data obtained near one end S of the imaging area on the imaging object using an average value for the positions corresponding to the second detection data S11 to S18, S21 to S28, S71 to S78, and S81 to S88 along the channel direction x obtained before the start of scanning. The system similarly corrects the first detection data obtained near the other end E of the imaging area on the imaging object using an average value for the positions corresponding to the second detection data E'11 to E'18, E'21 to E'28, E'71 to E'78, and E'81 to E'88 along the channel direction x obtained after the start of scanning. In addition, it may be preferable to find a weighted average for the positions corresponding to the second detection data S11 to S18, S21 to S28, S71 to S78, S81 to S88, E'11 to E'18, E'21 to E'28, E'71 to E'78, and E'81 to E'88 obtained before the start of scanning or after the end of scanning along the channel direction x.

The central processing unit 30 reconstructs the image based on the corrected first detection data, then allows the display apparatus 32 to display the reconstructed image.

According to the embodiment, as mentioned above, the X-ray detection array 23 obtains the first detection data using the X-ray detection elements 23 corresponding to the area not shielded by the collimator 22. In this case, the first detection data is generated by: the X-ray 5 directly irradiated to the X-ray detection elements 23a from the X-ray tube 20 through the imaging object 6; and the X-ray 5 as a scattered radiation from the X-ray tube 20 through the imaging object 6. Further, the X-ray detection array 23 obtains the second detection data using the X-ray detection elements 23a corresponding to the area shielded by the collimator 22. In this case, the second detection data is generated by the X-ray as a scattered radiation from the X-ray tube 20 through the imaging object. The central processing unit 30 having the tomographic image generation means corrects the first detection data based on the detection data including the first and second detection data. Finally, the central processing unit 30 generates a tomographic image for the imaging area R of the imaging object 6.

Accordingly, the embodiment can prevent the tomographic image contrast from degrading, prevent artifact from occurring, and improve the tomographic image quality.

The helical scanning system according to the embodiment helically scans the X-ray 5 around the imaging object 6 along the body axis direction z from one end S to the other end E along the body axis direction z of the imaging area R on the imaging object 6. At the start and the end of scanning, this helical scanning system aligns the center of the X-ray detection array 23 along the body axis direction with one end S or the other end E of the imaging area R on the imaging object 6 along the body axis direction. The system controls the collimator 22 to shield the X-ray 5 incident on the areas SS and SE opposite to the imaging area R with reference to the center of the X-ray detection array 23 along the body axis direction z. In this manner, the system obtains the first and second detection data as detection data. That is, the collimator 22 partly shields the X-ray 5 irradiated from the X-ray tube 20 at the start and the end of scanning. More specifically, the collimator 22 shields the X-ray 5 incident on the areas SS and SE opposite to the imaging area R with reference to the center of the X-ray detection array 23 along the body axis direction z. In addition, the system obtains the second detection data generated by the X-ray as the scattered radiation at the specified areas SS and SE shielded by the collimator 22 on the X-ray detection array.

In the helical scanning system according to the embodiment, the collimator controller 26 controls the collimator 22 so as to widen the range of irradiating the X-ray 5 compared to at the start or the end of scanning. This control is provided when the scan takes place from one end S to the other end E of the imaging area R on the imaging object 6 along the body axis direction z. The tomographic image generation means of the central processing unit 30 corrects the first detection data using the second detection data. At this time, the first detection data is obtained correspondingly to the imaging area R on the imaging object 6 from one end S to the center E along the body axis direction z. The second detection data is obtained at the start or the end of scanning. The system uses the corrected first detection data to generate a tomographic image for the imaging area R on the imaging object 6. The embodiment obtains more first detection data while scanning the imaging area R on the imaging object 6 from one end S to the other end E along the body axis direction than those obtained at the start or the end of scanning. The obtained first detection data is used for tomographic image generation.

Accordingly, the embodiment enables the helical scanning system to effectively use the X-ray 5 from the X-ray tube 20. It is possible to prevent the tomographic image contrast from degrading, prevent artifact from occurring, and improve the tomographic image quality.

The axial scanning system according to the embodiment scans around the imaging object 6 from one end S to the other end E of the imaging area R on the imaging object 6 on a section basis. The system controls the collimator 22 before the start of scanning or after the end of scanning so that the X-ray is not irradiated to specified elements of the X-ray detection array 23 near one end S or the other end E of the imaging area R on the imaging object 6 along the body axis direction z. In this manner, the system obtains the first and second detection data as detection data. Here, the scan takes place from one end S to the other end E of the imaging area R on the imaging object 6 along the body axis direction z. At this time, the collimator controller 26 controls the collimator 22 so as to widen the range of irradiating the X-ray 5 compared to before the start of scanning or after the end of scanning. The tomographic image generation means of the central processing unit 30 corrects the first detection data using the second detection data. At this time, the first detection data is obtained correspondingly to the imaging area R on the imaging object 6 from one end S to the center E along the body axis direction z. The second detection data is obtained before the start of scanning or after the end of scanning. The system uses the corrected first detection data to generate a tomographic image for the imaging area R on the imaging object 6. The embodiment obtains more first detection data while scanning the imaging area R on the imaging object 6 from one end S to the other end E along the body axis direction than those obtained before the start of scanning or after the end of scanning. The obtained first detection data is used for tomographic image generation.

Accordingly, the embodiment also enables the axial scanning system to effectively use the X-ray 5 from the X-ray tube 20. It is possible to prevent the tomographic image contrast from degrading, prevent artifact from occurring, and improve the tomographic image quality.

According to the embodiment, the tomographic image generation means of the central processing unit 30 uses an average value of the second detection data to correct the first detection data. The tomographic image generation means uses the corrected first detection data to generate a tomographic image for the imaging area on the imaging object.

Consequently, even if the second detection data contains a noise component due to the X-ray 5 as a scattered radiation, the embodiment can accurately remove scattered radiation components from the first detection data using an average value of the second detection data and correct the first detection data. It is possible to prevent the tomographic image contrast from degrading, prevent artifact from occurring, and improve the tomographic image quality.

While there has been described the specific preferred embodiment of the present invention, it is to be distinctly understood that the present invention is not limited thereto but may be otherwise variously embodied within the spirit and scope of the invention.

For example, the above-mentioned embodiment obtains the first and second detection data using the radiation detection elements at the positions in the radiation detection array along the channel direction. The tomographic image generation means calculates an average value of the second detection data. The tomographic image generation means then calculates a difference between each of the first detection data and the average value of the second detection data to correct the first detection data. The corrected first detection data is used to generate a tomographic image for the imaging area. There may be an alternative to using an average value for each position in the radiation detection array along the channel direction. For example, the helical scanning system may calculate an average value for all the second detection data obtained at the start of scanning. The system may calculate a difference between each of the first detection data and the second detection data to correct each of the first detection data.

While there has been described the example of using the X-ray as a radiation in the above-mentioned embodiment, the present invention is not limited thereto. There may be used the other radiations such as gamma rays, for example.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiation tomography apparatus comprising:
    an X-ray irradiation device for irradiating an X-ray while scanning helically around an imaging area of an imaging object on a body axis of said imaging object;
    an X-ray detection array comprising X-ray detection elements arranged in an array for detecting said X-ray and for generating detection data according to said X-ray detected by said X-ray detection elements;
    an irradiation range adjustment device disposed between said X-ray irradiation device and said X-ray detection array for shielding said X-ray to adjust an irradiation range of said X-ray so that said X-ray is not irradiated to a specified area of said X-ray detection array;
    a controller for controlling at least said irradiation range adjustment device; and
    a tomographic image generation device for generating a tomographic image of said imaging area of said imaging object based on said detection data;
    wherein said detection data of said X-ray detection array comprises first and second detection data, said first detection data results from said X-ray detected by said X-ray detection element corresponding to an area not shielded by said irradiation range adjustment device, and said second data results from said X-ray detected by said X-ray detection element corresponding to an area shielded by said irradiation range adjustment device during at least one of a beginning and an end of said helical scanning;
    an opening of said irradiation range adjustment device is adjustable during said helical scanning to shield said X-ray during at least one of the beginning and the end of said helical scanning to shield at least a part of an area outside of said imaging area along the body axis, wherein said opening is adjusted by said controller during said helical scanning such that, upon helical scanning of said imaging area from a first end to an opposing second end in a direction along said body axis, said irradiation range adjustment device makes the irradiation range of said X-ray wider than an irradiation range during at least one of the beginning and the end of said helical scanning; and
    said tomographic image generation device correcting said first detection data by using said second detection data from said X-ray detected during at least one of the beginning and the end of said helical scanning, and generating said tomographic image based on a corrected first detection data.

2. The radiation tomography apparatus according to claim 1, wherein a center of said X-ray detection array is oriented with respect to said body axis to align said X-ray detection array at one of the first end and the second end of said imaging area along said body axis such that said irradiation range adjustment device shields said area outside of said imaging area from said X-ray during at least one of the beginning and the end of said helical scanning.

3. The radiation tomography apparatus according to claim 1, wherein in said first and second detection data obtained by said X-ray detection elements arranged correspondingly to positions in said radiation detection array along a channel direction, said tomographic image generation device calculates an average value of said second detection data, calculates a difference between each of said first detection data and said average value of said second detection data to correct each of said first detection data, and generates a tomographic image for said imaging area using said corrected first detection data.

4. A radiation tomography apparatus comprising:
    an X-ray irradiation device for irradiating an X-ray while scanning around an imaging area of an imaging object on a body axis of said imaging object with more than one rotation;
    an X-ray detection array comprising X-ray detection elements arranged in an array for detecting said X-ray and for generating detection data according to said X-ray detected by said X-ray detection elements;
    an irradiation range adjustment device which is disposed between said X-ray irradiation device and said X-ray detection array for shielding said X-ray to adjust an irradiation range of said X-ray so that said X-ray is not irradiated to a specified area of said X-ray detection array;
    a controller for controlling at least said irradiation range adjustment device; and
    a tomographic image generation device for generating a tomographic image of said imaging area of said imaging object based on said detection data;
    wherein said detection data of said X-ray detection array comprises first and second detection data, said first detection data results from said X-ray detected by said X-ray detection element corresponding to an area not shielded by said irradiation range adjustment device, and said second data results from said X-ray detected by said X-ray detection element corresponding to an area shielded by said irradiation range adjustment device during at least one of a first rotation and a last rotation of said scanning;
    an opening of said irradiation range adjustment device is adjustable during said scanning to shield said X-ray during at least one of the first rotation and the last rotation of said scanning with more than one rotation to shield at least a pan of an area outside of said imaging area along the body axis, wherein said opening is adjusted by said controller during said scanning such that, upon scanning of said imaging area from a first end to an opposing second end in a direction along said body axis, said irradiation range adjustment device makes the irradiation range of said X-ray wider than an irradiation range during at least one of the first rotation and the last rotation of said scanning; and said tomographic image generation device correcting said first detection data by using said second detection data from said X-ray detected during at least one of the first rotation and the last rotation of said scanning, and generating said tomographic image based on a corrected first detection data.

5. The radiation tomography apparatus according to claim 4, wherein said first and second detection data obtained by said X-ray detection elements arranged correspondingly to positions in said X-ray detection array along a channel direction, said tomographic image generation device calculates an average value of said second detection data, calculates a difference between each of said first detection data and said average value of said second detection data to correct each of said first detection data, and generates a tomographic image for said imaging area using said corrected first detection data.

6. The radiation tomography apparatus according to claim 4, wherein said irradiation range adjustment device shields said X-ray in a narrower irradiation range during at least one of the first rotation and the last rotation than other rotations.

7. The radiation tomography apparatus according to claim 4, wherein a center of said X-ray detection array in said body axis direction is aligned with one of the first end and the second end of said imaging area along said body axis such that said irradiation range adjustment device shields said area outside of said imaging area from said X-ray during at least one of the first rotation and the last rotation of said scanning.

* * * * *